(12) United States Patent
Chudoba et al.

(10) Patent No.: US 7,050,911 B1
(45) Date of Patent: May 23, 2006

(54) METHOD OF IDENTIFYING CHANGES IN BIOPOLYMERS

(75) Inventors: Ilse Chudoba, Altlussheim (DE); Thomas Loerch, Reilingen (DE); Andreas Plesch, Schwetzingen (DE)

(73) Assignee: Metasystems, Hard & Software GmbH, Altlussheim (DE)

( * ) Notice: Subject to any disclaimer, the term of this patent is extended or adjusted under 35 U.S.C. 154(b) by 255 days.

(21) Appl. No.: 09/250,466

(22) Filed: Feb. 16, 1999

(30) Foreign Application Priority Data

Feb. 16, 1998 (DE) ............... 198 06 303
Nov. 3, 1998 (DE) ............... 198 50 661

(51) Int. Cl.
*G06F 19/00* (2006.01)
*G01N 33/58* (2006.01)

(52) U.S. Cl. .................... 702/32; 436/172; 435/6

(58) Field of Classification Search ......... 435/6, 435/91.2, 287.2; 536/24.3; 436/172, 800

See application file for complete search history.

(56) References Cited

U.S. PATENT DOCUMENTS

| | | | | |
|---|---|---|---|---|
| 5,107,422 A | * | 4/1992 | Kamentsky et al. ... | 364/413.08 |
| 5,784,162 A | * | 7/1998 | Cabib et al. ............... | 356/456 |
| 5,817,462 A | * | 10/1998 | Garini et al. ................. | 435/6 |
| 6,458,584 B1 | * | 10/2002 | Mirzabekov et al. .... | 435/287.2 |

FOREIGN PATENT DOCUMENTS

WO    WO 96/262291    8/1996

OTHER PUBLICATIONS

Shalon et al. A DNA microarray ssytem for analyzing complex DNA samples using two-color fluorescent probe hybridization. Genome Research. (1996), vol. 6, No. 7, pp. 639-645.*

* cited by examiner

*Primary Examiner*—Marjorie A. Moran
(74) *Attorney, Agent, or Firm*—J. Herbert O'Toole; Nexsen Pruet, LLC

(57) ABSTRACT

The current invention relates to a method of identifying changes in biopolymers, especially in chromosomal DNA, using two or more different sets of labelled detector molecules, as well as to a diagnostic kit for detecting these changes.

50 Claims, 4 Drawing Sheets

Fig. 2

| region-specific DNA library | Cy 5 | TR | Cy 5.5 | SO | SG |
|---|---|---|---|---|---|
| 1 | ■ | | | | |
| 1/2 | □ | □ | | | |
| 2 | | ■ | | | |
| 2/3 | | □ | □ | | |
| 3 | | | ■ | | |
| 3/4 | | | □ | □ | |
| 4 | | | | ■ | |
| 4/5 | | | | □ | □ |
| 5 | | | | | ■ |
| 5/6 | □ | | □ | | □ |
| 6 | ■ | | ■ | | |

METHOD OF IDENTIFYING CHANGES IN BIOPOLYMERS

FIELD OF THE INVENTION

The present invention relates to a method of identifying changes in biopolymers, especially in chromosomal DNA, using two or more different sets of labelled detector molecules, as well as to a diagnostic kit for detecting these changes.

BACKGROUND OF THE INVENTION

The representation of human chromosomes has been carried out so far with banding techniques which permit a specific recognition of the chromosomes using light and dark bands (e.g. G-banding, O-banding, R-banding). These banding techniques are based on methods developed by Caspersson et al., (Exp. Cell Res. 80, 1970, 315–319), Sumner et al. (Nature 232, 1971, 31), Seabright et al. (Lancet 2, 1971, 971–972) and Dutrillaux et al. (C R Acad. Sci., Paris, 272, 1971, 3636–3640). However, the identity of individual chromosomal bands can not be defined in every instance with these methods since all bands of all chromosomes appear only either light or dark. This turns out to be a significant disadvantage since chromosomes can be very different morphologically from cell to cell and from tissue to tissue and can possibly comprise translocations (e.g., in the case of tumors) the recognition of which can be of particular significance for the person to be examined. This applies, e.g., to the decision whether or not to have children in the case of a parent having balanced translocations ("crossing-overs" or "exchanges of parts of chromosomes"), to the recognition of the cause of abnormalities in children with and without mental retardation, and to the diagnosis of leukemias and other tumors which frequently exhibit specific chromosomal changes with diagnostic and therapeutic significance.

Fluorescence in-situ hybridization (FISH) was described for the first time for routine use in practicable form by Pinkel et al. (Proc. Natl. Acad. Sci. USA 83, 1986, 2934–2938) as a suggestion for solving this problem. Today, all human chromosomes of a metaphase can be represented in different colors with this method by using chromosome-specific DNA libraries (chromosome painting, 24-color FISH, Schröck et al., Science 273, 1996, 496497; Speicher et al., Nature Genet. 12, 1996, 368–376). Through the use of vectors, e.g., cosmids, pacs or YACs, which can contain different amount of human DNA, specific chromosomal regions can be re-checked with respect to their integrity via multicolor techniques by means of FISH. Even parts of genes and repetitive DNA elements can be identified in this way regarding their chromosomal localization and their presence or absence. However, a multicolor representation of chromosomal sections at the band level has not been possible so far.

Thus, the problem underlying the current invention is to provide a novel and improved method for the identification of, in particular, changes in chromosomal DNA which method enables a multicolor representation at the band level.

This problem is solved by the embodiments of the present invention characterized in the claims.

DETAILED DESCRIPTION OF THE INVENTION

In particular, a method of identifying changes in biopolymers as target molecules using two or more different sets of labelled detector molecules is provided in which at least two sets are specific for a certain region in the target molecules and the labels of the particular detector molecules of these sets specific for a certain region in the target molecules are different, the method comprising the steps of
(a) carrying out bonding reactions between the detector molecules of the different sets and the target molecules, wherein the particular labelled detector molecules of at least two sets bond in such a manner to a certain region of the target molecules that the different labels of the detector molecules overlap, and
(b) qualitatively and quantitatively evaluating the bondings obtained in this manner via the different labels of the detector molecules.

The term "biopolymers as target molecules" means DNA (preferably chromosomal DNA), RNA, or polypeptides. The target molecules may be appropriately arranged or immobilized prior to carrying out the method of invention, in particular prior to step (a), e.g., by gel electrophoretic separation in a suitable matrix or fixing or arranging, e.g., metaphase chromosomes or interphase nuclei on a suitable carrier.

The term "labelled detector molecules" means nucleic acids or antibodies having at least one label. The antibodies may be present polyclonally or monoclonally. The terms "nucleic acid" and "nucleic-acid sequence" and "nucleic-acid probes" mean native, semisynthetic, or modified nucleic-acid molecules of deoxyribonucleotides and/or ribonucleotides and/or modified nucleotides such as amino nucleotides or ($\alpha$-S)-triphosphate nucleotides. In a preferred embodiment of the current invention the nucleic acids stem from chromosomal DNA from, e.g., mammals such as *homo sapiens sapiens*. The chromosomal DNA as detector molecules is present in vectors, e.g., cosmids or YACs, or stems from chromosomal or chromosome region-specific DNA libraries which can be obtained, e.g., via microdissection methods or laser-activated flow-cytometric sorting of specific chromosomes and, if required, subsequent amplification by, e.g., DOP-PCR.

The term "labels" means suitable directly or indirectly detectable atoms or molecules which are introduced into the detector molecules or connected to them. Suitable labels are, e.g., those comprising fluorescent dyes coupled to nucleotides and/or those comprising, e.g., biotin and/or digoxigenin and/or nucleotides labelled with radioactive isotopes. In a preferred embodiment the labelling compound is a fluorescent dye having a difference, sufficient for the selection of small amounts of substance, in the fluorescence behavior of the emission spectra such as, e.g., cumarins and rodamins, and/or in the fluorescence lifespan such as, e.g., fluorescent isothiocyanates and europium-chelate-labelled and/or porphyrin-labelled avidines.

The term "bonding reaction" means a hybridization, preferably an in situ hybridization, or an antigen/antibody reaction dependent on the selection of the detector molecules and/or of the target molecules. The term "in situ hybridization" means the apposition of a synthetically produced DNA and/or RNA molecule provided with biological, physical or chemical labels for detection as detector molecule to native DNA and/or RNA sequences occurring in nature, wherein the apposition is achieved by denaturing and renaturing the appropriate nucleic acids. Of course, these DNA and/or RNA probes contain at least one sequence section capable of hybridizing with a DNA and/or RNA sequence of the target molecule, such as a chromosome. This sequence section comprises a specific, individually present sequence region of the detector molecule which region is preferably 100 to 1,000 base pairs long and which apposes itself to a complementary region of the target molecule through the formation of hydrogen bridges at a suitable temperature, preferably at 50° C. or less, and at a suitable saline concentration comprising preferably 50–300 mmol/l monovalent ions and 0–10 mmol/l bivalent ions. The bonding reaction of the particular sets of labelled detector molecules may be carried out simultaneously or successively.

The expression "set of detector molecules" means detector molecules which are specific for a certain region of the target molecules. This set of detector molecules may be, e.g., chromosomal DNA present in vectors or may be a chromosome-specific DNA library. The labels of the detector molecules in the set may be the same or different, e.g., three different labels.

The expression "at least two or more different sets of labelled detector molecules" means the presence of at least one pair of different sets, wherein the sets of this pair bond in a certain area or region of the target molecules in such a manner that at least the different labels of the particular detector molecules, preferably the bonding sites of the particular detector molecules of these different sets, overlap. This property, according to the invention, of a pair of different sets means that the particular detector molecules in the different sets of a pair which are produced or obtained in an overlapping manner from this certain region of the target molecules can be used as a standard or for comparative examination with appropriately processed specimens from patients. In an embodiment according to the invention the detector molecules of a set are preferably designed in such a manner that after the hybridization the detector molecules are bound in a continuously changed concentration, preferably in the manner of a Gauss distribution, in the longitudinal direction to the target molecules, e.g., chromosomes.

The qualitative and quantitative evaluation of the bondings obtained in step (a) via the different labels of the detector molecules, which evaluation is characterized in step (b) of the method according to the invention, may be accomplished by employing a scanning device or a device for directed scanning, e.g., along or in the longitudinal direction of the chromosome to be investigated. Such a scanning device is, e.g., a fluorescence microscope. Image-generating signals can be taken by the scanning device via an image processing unit, e.g., a CCD camera, via the physical and/or chemical and/or biological labels of the detector molecules which have been apposed to the desired target molecules. This image processing unit processes the individual signals of the different labels in a suitable manner supported by a computer. The intensities and/or the intensity relationships of the different labels in the regions of overlapping and non-overlapping labels of the particular detector molecules can be recorded and evaluated qualitatively and quantitatively, preferably in the longitudinal direction of the target molecules, particularly of fixed metaphase chromosomes, with this image processing unit coupled to the scanning device.

Further subject matter of the current invention comprises a diagnostic kit for the identification of changes in biopolymers, as defined herein, as target molecules, the kit containing at least two different sets of labelled detector molecules in accordance with definitions set forth above.

In particular, the kit according to the invention can be used for the identification or exclusion of chromosomal aberrations in human genetics such as balanced chromosome rearrangements which are, as is known, of great significance for (a) the decision whether or not to have children, in the case of carriers of such a change; (b) balanced and unbalanced chromosome changes as the cause of malformations and/or mental retardation; and (c) in the tumor diagnosis of solid tumors as well as of hematological neoplasias (AML, ALL, MDS, and others), on the one hand for the detection of known alterations relevant to prognosis and on the other hand for the determination of further, previously unknown alterations.

Further subject matter of the current invention relates to an automatic imaging correction by addition of a localized DNA probe.

A monochrome CCD camera in combination with specific fluorescence filters is used when recording chromosome region-specific specimens labelled with different fluorochromes like the specimens used for the methods of multi-color banding. The signals of the individual fluorochromes are recorded successively as individual images and subsequently combined to a color image. A shift of the position of the individual images relative to each other on account of optical influences of the filters (different wedge errors, parallel shift due to slight tilting in the path of the rays) can not be excluded thereby. An interactive or automatic correction, e.g., by a correlation of the individual images, is not possible with the required precision because the at most partially overlapping probes do not have any common structures which can be used for a subsequent superpositioning. Every slight shift results in the evaluation of the intensity ratios in artifacts in the banding pattern.

An automatic correction is made possible by adding a localized DNA probe which is simultaneously labelled with all fluorochromes used in the method according to the invention. A structure which is identical in all individual images is therefore available for the automatic correction of position. The correction of position may take place, e.g., via a determination of the center of intensity of the probe in each individual image and by a subsequent relative shifting of the individual images in such a manner that the centers of the individual images come to be located at the same position.

Additionally, distortions of the images relative to each other can be determined and corrected by the use of two different multi-labelled probes.

The use of even more probes basically makes possible the correction of more complex transformations of position than translation and rotation such as, e.g., changes of scale.

Furthermore, it can be advantageous in a further preferred embodiment of the current invention to add calibrating probes (DNA probes or fluorescent particles) of known intensity which can serve for standardizing the intensities of the fluorescent signals to be evaluated.

Furthermore, it can be advantageous in a further preferred embodiment of the current invention to add DNA probes whose exact localization within the genome is known and which can be used for establishing the relation between color bands and the ISCN bands.

BRIEF DESCRIPTION OF THE DRAWINGS

FIG. 2 is a tabular presentation of the label pattern of the region-specific chromosome section of chromosome 5 shown in FIG. 1. Cy5, TR (Texas red), Cy5.5, SO (spectrum orange), SG (spectrum green) are the different fluorescent dyes which were used to label the individual region-specific DNA libraries. The association is characterized by a solid square: ("). The labellings resulting from the overlapping of the DNA libraries in the corresponding regions are rendered recognizable by an empty square (u).

EXAMPLE

The following example explains the invention.

A total of seven overlapping chromosome microdissection region-specific libraries were produced for the multicolor band pattern of chromosome 5 (Meltzer et al., Nature Genet. 1, 1992, 24–26). The p arm of chromosome 5 was subdivided for this into two regions, the q arm into four regions. Eight to ten fragments per chromosome region were isolated with a finely drawn-out glass needle from the microscope slide under microscopic view (Senger et al., Hum, Genet. 84, 1990, 507–511). The thus obtained DNA was amplified via a DOP-PCR (degenerate oligonucleotide polymerase chain reaction, Telenius et al., Genomics 13, 1992, 718–725; Zhang et al., Blood 81, 1993, 3365–3371). In a subsequent reaction these chromosome region-specific DNA libraries were partially labelled directly with fluorochromes coupled to nucleotides (e.g., Spectrum Orange-dUTP, Spectrum Green-dUTP, both Vysis and Texas Red-dUTP, Molecular Probe). In another part, DNA libraries were labelled with nucleotides coupled to haptenes (e.g., biotin-dUTP and digoxigenin-dUTP, Boehringer, Mannheim). After the hybridization has taken place haptenes can be detected with suitable detection reagents (e.g., avidine-Cy5, Amersham, and anti-digoxigenin IgG, Boehringer, Mannheim, which is coupled to Cy5.5, Mab labeling kit, Amersham).

The hybridization, washing steps, and detection are carried out according to standard protocols (Senger et al., Cytogenet. Cell Genet. 54, 1993, 49–53).

The analysis is carried out, e.g., with a fluorescence microscope equipped with suitable filter sets. Separate images are taken for each color channel, which images can be subsequently processed further with a computer.

A characteristic feature of the partial "painting" probes obtained by microdissection is a continuously weakening fluorescent signal in the border regions. A simultaneous overlapping of the probes and, therefore, of the fluorescent signals of two adjacent partial "painting" probes brings about a constantly changing ratio of the fluorescence intensities along chromosome 5. If a chromosome stained in this manner is subdivided into several (20–25) small sections, a false color stain can be assigned to each of these sections via a suitable computer program on the basis of the relative fluorescence intensities of all fluorochromes used. This assignment gives rise to a colored band pattern along a chromosome, in this case chromosome 5. The same combination of fluorescence relationships and false colors can be used for all further hybridizations with the same specimen set.

Figure 1:
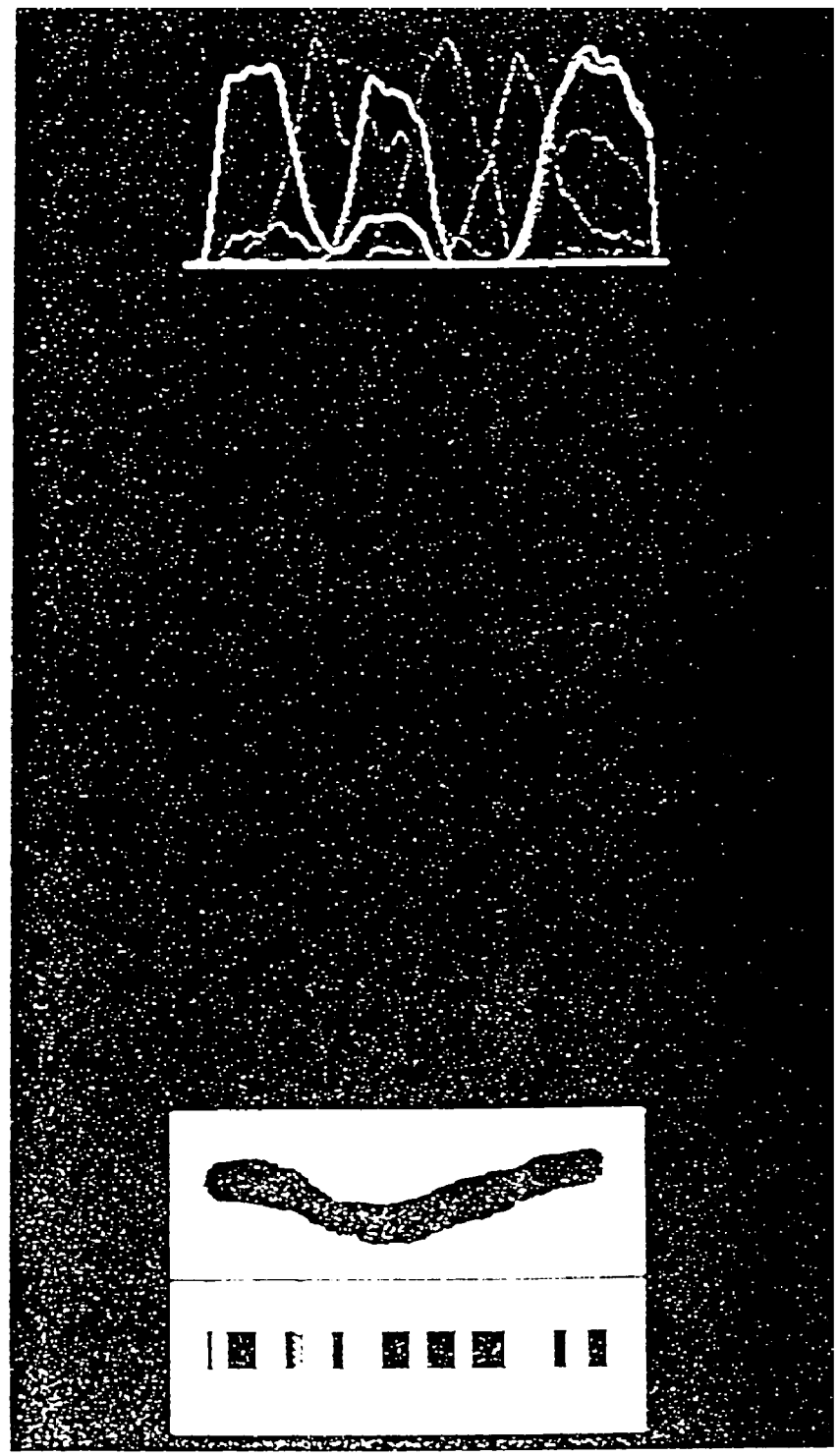
FIG. 1 is a photographic representation for the qualitative and quantitative evaluation of the localization of region-specific colorations in chromosome 5. In the upper part of this figure the distribution of the labelled detector molecules in the longitudinal direction of the chromosome as well as intensities of the different labels of the detector molecules are shown graphically.
Figure 3:
FIG. 3 shows the respective homologous normal chromosomes 5 from two different metaphase plates with multicolored banding. The presentation makes it clear that the banding pattern is identical on the homologous chromosomes and can even be reproduced from metaphase plate to metaphase plate.

Since the hybridization behaves in a sufficiently constant manner the band pattern is also correspondingly reproducible (FIG. 3). A loss of the resolving power in the case of shorter chromosomes, as is known from previous customary banding methods (e.g., GTG banding) is not observed in this case. A reproducible pattern of at least 25 bands is achieved for chromosome 5. This corresponds to a band level of approximately 550 bands per haploid chromosome set.

Figure 5:
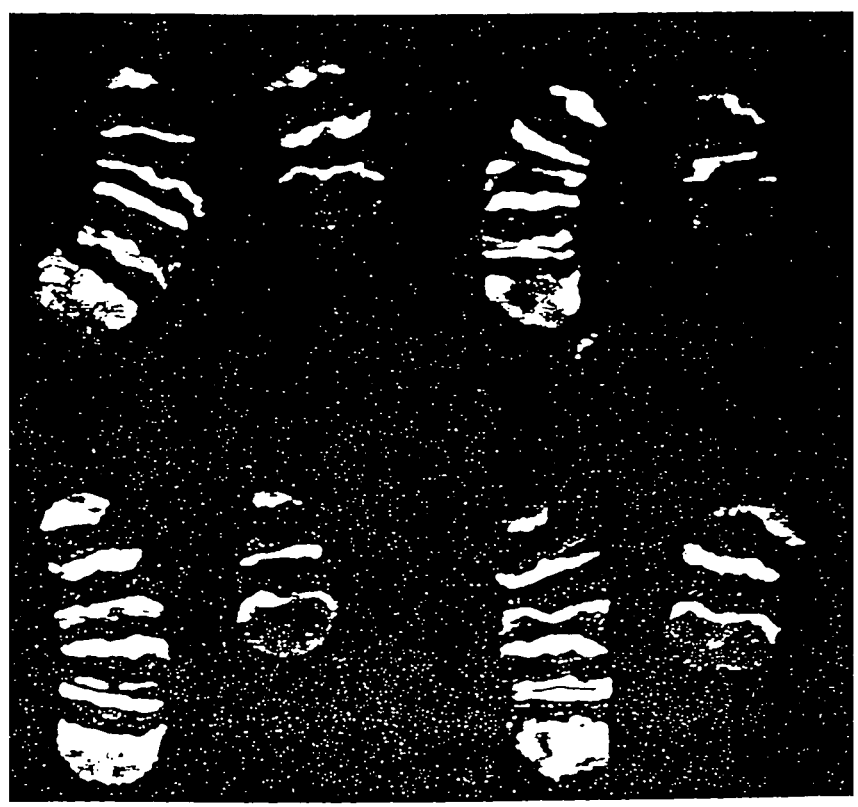
FIG. 5 shows chromosomes 5 in a case of acute myeloid leukemia. The normal chromosome 5 is shown on the right side and the chromosome on the left side displays an interstitial deletion in the long arm.
Figure 4:
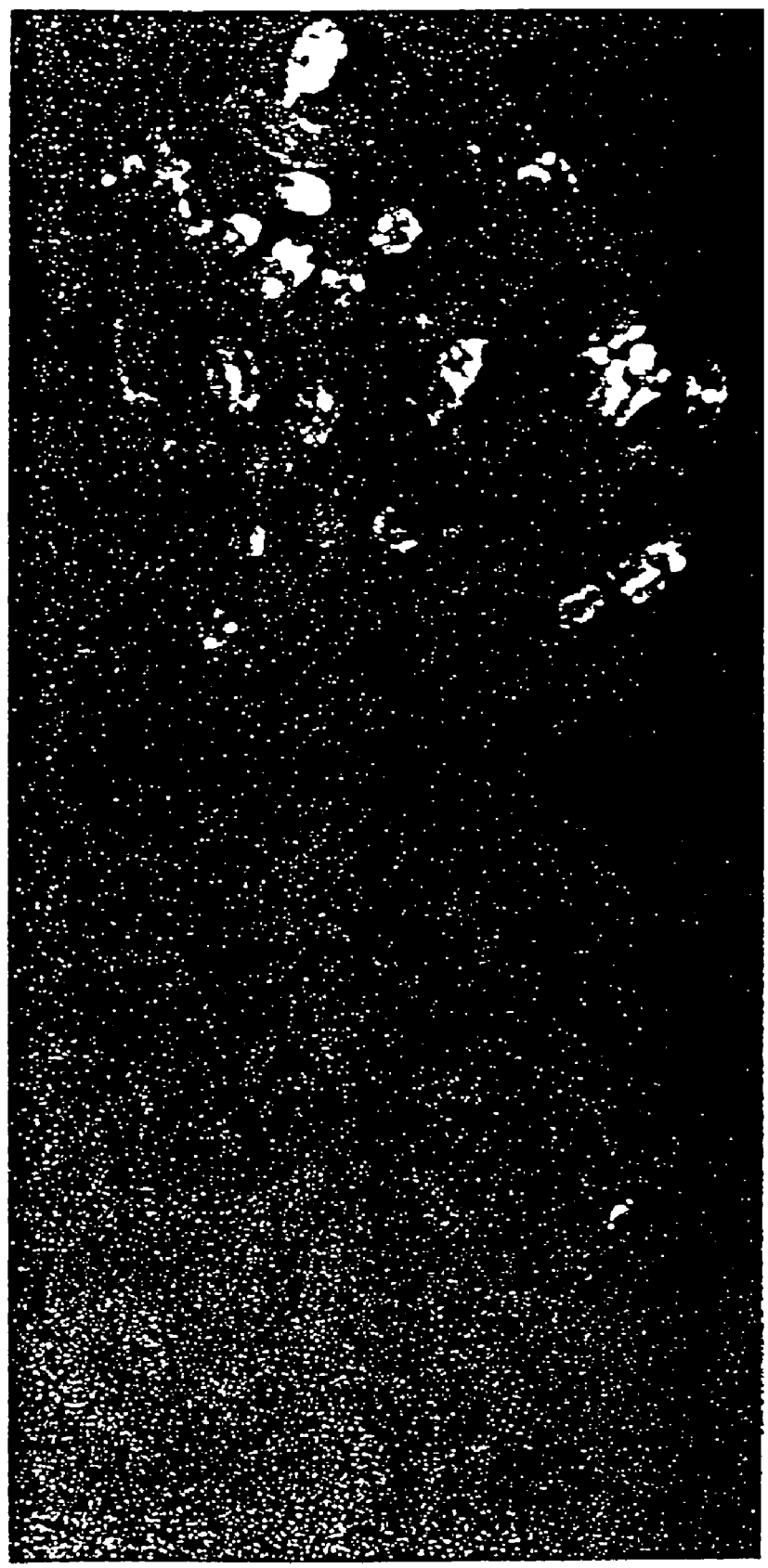
FIG. 4 shows a photographic representation of a multicolored FISH of a metaphase plate with complex chromosomal aberrations.

It is possible with the aid of this method to identify changes in chromosomes independently of their condensation state. This is particularly significant in tumor cytogenetics, too. Tumor chromosomes often display a low resolution of the band pattern, which makes the recognition of chromosomal changes significantly difficult. It is therefore to be assumed that previously unknown cytogenetic changes are present in tumors, which possibly represent an important prognosis factor and could therefore be of significance, e.g., for a risk-adapted therapy. According to the invention at least 25 bands can be achieved even on tumor chromosomes after hybridization with the specimen set for chromosome 5 described in detail above (FIG. 5).

What is claimed is:

1. A method of identifying differences between biopolymers, the method comprising the steps:
    a) providing at least one pair of different sets of labeled detector molecules wherein the different sets of labeled detector molecules of one pair are specifically bondable to a certain region in said biopolymers; and the labels of the one set of labeled detector molecules of said one pair differs from the labels of another one set of labeled detector molecules of said one pair;
    b) exposing said labeled detector molecules to said biopolymers under conditions permitting bonding reactions to occur between said labeled detector molecules and said biopolymers; wherein said one set of labeled detector molecules of said one pair binds to a certain region of the biopolymer overlapping with the certain region bound by said another one set of labeled detector molecules of said one pair;
    c) recording the presence, intensity and intensity ratios of the labeled detector molecules at selected regions of said biopolymers by scanning the biopolymers in longitudinal direction using a scanning device;
    d) evaluating the recorded intensities and intensity ratios, whereby the biopolymer is divided into a number of sections and by means of an appropriate calculation program, a false color is assigned to each of these sections based on the relative intensity ratios; and
    e) identifying differences between said biopolymers by comparing the result to that obtained for a different biopolymer, wherein the bonded labeled detector molecules of one set display a continuously changing label-signal intensity along the longitudinal direction of the biopolymer.

2. The method of claim 1, wherein the bonded labeled detector molecules of each of the different sets of one pair display a continuously changing label-signal intensity along the longitudinal direction of the biopolymer.

3. The method of claim 2, wherein the displayed continuously changing label-signal intensity along the longitudinal direction results from a continuously changing concentration of each of the different sets of bonded labeled detector molecules of one pair along the longitudinal direction of the biopolymer.

4. The method of claim 3, wherein the continuously changing concentration of each of the different sets of bonded labeled detector molecules of one pair is distributed along the longitudinal direction in a Gaussian distribution.

5. The method of claim 1, wherein the biopolymers are immobilized at least before step (b).

6. The method of claim 5, wherein the biopolymers are immobilized on a carrier or in a matrix.

7. The method of claim 1, wherein said bonding reactions between each of said labeled detector molecules and said biopolymer are carried out simultaneously or successively.

8. The method of claim 1, wherein said bonding reaction in step (b) is selected from the group consisting of a nucleic acid hybridization and an antigen/antibody reaction.

9. The method of claim 8, wherein said nucleic acid hybridization is an in situ hybridization.

10. The method of claim 1, wherein said biopolymers are selected from the group consisting of nucleic acids and polypeptides.

11. The method of claim 10, wherein said nucleic acids are DNA or RNA.

12. The method of claim 10, wherein said nucleic acids are chromosomal DNA.

13. The method of claim 1, wherein the labeled detector molecules are selected from the group consisting of nucleic acids and antibodies.

14. The method of claim 13, wherein said different nucleic acids are selected from different chromosome region-specific DNA libraries.

15. The method of claim 1, wherein the label comprises a fluorescent dye.

16. The method of claim 1, wherein said step (a) further comprises providing at least one set of a localized calibrating probe, said probe comprising calibrating labels.

17. The method of claim 16, wherein said calibrating labels comprise all of said labels of said labeled detector molecules of the different sets of at least one pair.

18. The method of claim 1, wherein said step (a) further comprises providing a number of localized calibrating probes, said number being one less than the total number of said labels in said labeled detector molecules, each of said probes comprising two labels; and said step (d) further comprises correcting registration errors between individual images corresponding to individual labels, said registration errors being introduced by changing filters between the acquisition of said individual images; said correcting step being achieved by pairwise comparison of the positions of the two labels of said calibrating probes.

19. The method of claim 18, wherein said step (d) further comprises forming images of said biopolymers; and aligning said images with respect to said bondings, thereby providing positional correction for said bondings.

20. The method of claim 19, wherein said calibrating probes are used for positional correction of said bondings.

21. The method of claim 18, wherein said step (a) further comprises providing a plurality of said calibrating probes; and said step (d) further comprises correcting positional transformations of said bondings by comparison of the position of the labels of said calibrating probes.

22. The method of claim 21, wherein said step of correcting is automatic.

23. The method of claim 21, wherein said labels of said calibrating probes have known or reproducible constant intensity whereby the signal intensities of all of said labels can be standardized.

24. The method of claim 23, wherein said calibrating probes are fluorescence-labeled probes.

25. The method of claim 23, wherein said calibrating probes are fluorescence-labeled particles.

26. A method of identifying differences between biopolymers, the method comprising the steps:
    a) providing at least two different sets of labeled detector molecules wherein at least two sets of said labeled detector molecules at a time are specifically bondable to a certain region in said biopolymers; and the labels of said labeled detector molecules of one of said at least two sets differ from the labels of said labeled detector molecules of another of said at least two sets;
    b) exposing said labeled detector molecules to said biopolymers under conditions permitting bonding reactions to occur between said labeled detector molecules and said biopolymers; wherein the labeled detector molecules of said one of said at least two sets binds to a certain region of the biopolymer overlapping with the certain region bound by said labeled detector molecules of another of said at least two sets;
    c) recording the presence, intensity and intensity ratios of the labeled detector molecules at selected regions of said biopolymers by scanning the biopolymers in longitudinal direction using a scanning device;
    d) evaluating the recorded intensities and intensity ratios, whereby the biopolymer is divided into a number of sections and by means of an appropriate calculation program, a false color is assigned to each of these sections based on the relative intensity ratios; and
    e) identifying differences between said biopolymers by comparing the result to that obtained for a different biopolymer, wherein the bonded labeled detector molecules of one set display a continuously changing label-signal intensity along the longitudinal direction of the biopolymer.

27. The method of claim 26, wherein the bonded labeled detector molecules of each of the different sets display a continuously changing label-signal intensity along the longitudinal direction of the biopolymer.

28. The method of claim 27, wherein the displayed continuously changing label-signal intensity along the longitudinal direction results from a continuously changing concentration of each of the different sets of bonded labeled detector molecules along the longitudinal direction of the biopolymer.

29. The method of claim 28, wherein the continuously changing concentration of each of the different sets of bonded labeled detector molecules is distributed along the longitudinal direction in a Gaussian distribution.

30. The method of claim 26, wherein the biopolymers are immobilized at least before step (b).

31. The method of claim 30, wherein the biopolymers are immobilized on a carrier or in a matrix.

32. The method of claim 26, wherein said bonding reactions between each of said labeled detector molecules and said biopolymer are carried out simultaneously or successively.

33. The method of claim 26, wherein said bonding reaction in step (b) is selected from the group consisting of nucleic acid hybridization and an antigen/antibody reaction.

34. The method of claim 33, wherein said nucleic acid hybridization is an in situ hybridization.

35. The method of claim 26, wherein said biopolymers are selected from the group consisting of nucleic acids and polypeptides.

36. The method of claim 35, wherein said nucleic acids are DNA or RNA.

37. The method of claim 26, wherein said nucleic acids are chromosomal DNA.

38. The method of claim 26, wherein the labeled detector molecules are nucleic acids or antibodies.

39. The method of claim 38, wherein said different nucleic acids are selected from different chromosome region-specific DNA libraries.

40. The method of claim 26, wherein the label comprises a fluorescent dye.

41. The method of claim 26, wherein said step (a) further comprises providing at least one set of a localized calibrating probe, said probe comprising calibrating labels.

42. The method of claim 41, wherein said calibrating labels comprise all of said labels of said labeled detector molecules of the different sets.

43. The method of claim 26, wherein said step (a) further comprises providing a number of localized calibrating probes, said number being one less than the total number of said labels in said labeled detector molecules, each of said probes comprising two labels; and said step (d) further comprises correcting registration errors between individual images corresponding to individual labels, said registration errors being introduced by changing filters between the acquisition of said individual images; said correcting step being achieved by pairwise comparison of the positions of the two labels of said calibrating probes.

44. The method of claim 43, wherein said step (d) further comprises forming images of said biopolymers; and aligning said images with respect to said bondings, thereby providing positional correction for said bondings.

45. The method of claim 44, wherein said calibrating probes are fluorescence-labeled particles.

46. The method of claim 44, wherein said calibrating probes are used for positional correction of said bondings.

47. The method of claim 43, wherein said step (a) further comprises providing a plurality of said calibrating probes; and said step (d) further comprises correcting positional transformations of said bondings by comparison of the position of the labels of said calibrating probes.

48. The method of claim 47, wherein said step of correcting is automatic.

49. The method of claim 47, wherein said labels of said calibrating probes have known or reproducible constant intensity whereby the signal intensities of all of said labels can be standardized.

50. The method of claim 49, wherein said calibrating probes are fluorescence-labeled probes.

* * * * *